United States Patent
White

(10) Patent No.: US 7,983,750 B2
(45) Date of Patent: Jul. 19, 2011

(54) REFRACTORY PERIOD MANAGEMENT BASED ON DETECTION OF AN EVOKED RESPONSE

(75) Inventor: Harley White, Carnation, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 773 days.

(21) Appl. No.: 11/231,401

(22) Filed: Sep. 20, 2005

(65) Prior Publication Data

US 2007/0066999 A1  Mar. 22, 2007

(51) Int. Cl.
*A61N 1/362* (2006.01)
(52) U.S. Cl. ............................................................ 607/9
(58) Field of Classification Search .................. 607/4, 9, 607/28, 115
See application file for complete search history.

(56) References Cited

U.S. PATENT DOCUMENTS

| | | | |
|---|---|---|---|
| 4,343,311 A * | 8/1982 | Markowitz | 607/9 |
| 5,470,342 A * | 11/1995 | Mann et al. | 607/5 |
| 5,941,903 A | 8/1999 | Zhu et al. | |
| 6,324,422 B1 * | 11/2001 | Williams et al. | 600/510 |
| 6,553,259 B2 * | 4/2003 | Mouchawar et al. | 607/11 |
| 6,944,499 B2 | 9/2005 | Tang et al. | |
| 7,286,874 B1 | 10/2007 | Bornzin | |

* cited by examiner

*Primary Examiner* — Carl H Layno
*Assistant Examiner* — Brian T Gedeon
(74) *Attorney, Agent, or Firm* — Hollingsworth & Funk, LLC

(57) ABSTRACT

Various approaches are described for managing refractory periods based on the detection of an evoked response. The heart is paced and an evoked response is detected. At least one refractory period is adapted based on the detected evoked response. Adapting the refractory period may involve, for example, initiating a refractory period, terminating a refractory period, extending a refractory period or modifying one or more parameters of the refractory period. Adapting the refractory period may involve modifying a sensing threshold based on the detected evoked response. The sensing threshold of an atrial sensing channel may be adjusted, for example, to avoid sensing a ventricular evoked response on the atrial channel while allowing sensing of a P-wave on the atrial channel.

24 Claims, 8 Drawing Sheets

REFRACTORY PERIOD MANAGEMENT BASED ON DETECTION OF AN EVOKED RESPONSE

FIELD OF THE INVENTION

The present invention relates generally to cardiac rhythm management methods and devices and, more particularly, to managing refractory periods during cardiac pacing.

BACKGROUND OF THE INVENTION

The healthy heart produces regular, synchronized contractions. Rhythmic contractions of the heart are normally controlled by the sinoatrial (SA) node, specialized cells located in the upper right atrium. The SA node is the normal pacemaker of the heart, typically initiating 60-100 heart beats per minute. When the SA node is pacing the heart normally, the heart is said to be in normal sinus rhythm (NSR).

If heart contractions are uncoordinated or irregular, the heart is denoted to be arrhythmic. Cardiac arrhythmia impairs cardiac efficiency and can be a potential life threatening event. Cardiac arrhythmias have a number of etiological sources including tissue damage due to myocardial infarction, infection, or degradation of the heart's ability to generate or synchronize the electrical impulses that coordinate contractions.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid, uncoordinated contractions of the atria.

Bradycardia occurs when the heart rhythm is too slow. This condition may be caused, for example, by delayed impulses from the SA node, denoted sick sinus syndrome, or by a blockage of the electrical impulse between the atria and ventricles. Bradycardia produces a heart rate that is too slow to maintain adequate circulation.

Implantable cardiac rhythm management systems may include pacemakers, which have been used as an effective treatment for patients with serious arrhythmias. These systems typically comprise circuitry to sense signals from the heart and a pulse generator for providing electrical pulses to the heart. Leads extending into the patient's heart are connected to electrodes that contact the myocardium for sensing the heart's electrical signals and for delivering pulses to the heart.

Pacemakers deliver low energy electrical pulses timed to assist the heart in producing a contractile rhythm that maintains cardiac pumping efficiency. When a pace pulse produces a contraction in the heart tissue an electrical cardiac signal associated with the heart contraction is produced, denoted the evoked response.

Pace pulses may be intermittent or continuous, depending on the needs of the patient. There exist a number of categories of pacemaker devices, with various modes for sensing and pacing the heart. Single chamber pacemakers may pace and sense one heart chamber. A typical single chamber pacemaker is connected to a lead extending either to the right atrium or the right ventricle. Dual chamber pacemakers may pace and sense two chambers of the heart. A typical dual chamber pacemaker is typically connected to two leads, one lead extending to the right atrium and one lead to the right ventricle. Bi-ventricular or bi-atrial pacemakers may be used to provide pacing pulses to both the left and right ventricles or the left and right atria, respectively. Multi-chamber pacing, including bi-ventricular and/or bi-atrial pacing may be particularly advantageous for delivering cardiac resynchronization therapy for patient's suffering from congestive heart failure (CHF).

Pacemakers can be programmed to provide pace pulses to the heart on demand or at a fixed rate. When a pacemaker paces the heart at a fixed rate, the pacemaker provides pace pulses to the heart without taking into account the heart's spontaneous action. In contrast, pacemakers may sense the spontaneous activity of the heart and provide pace pulses synchronized to the spontaneous activity.

Rate adaptive pacemakers provide pacing at rates responsive to the patient's metabolic activity. Changes in metabolic activity may reflect exercise or non-exercise related changes, such as stress or excitement. The level of metabolic activity may be determined by sensing motion, respiratory rate, QT interval, venous oxygen saturation, temperature, or other patient conditions, for example. The pacemaker automatically adjusts the pacing rate to accommodate the sensed changes in the patient's condition.

Cardiac rhythm management systems may also include cardioverter/defibrillators to provide treatment for patients with serious cardiac tachyarrhythmias. The CRM system may sense cardiac activity and recognize an aberrant fast rhythm. Upon recognition of a tachyarrhythmia, the CRM system may automatically deliver one or a series of high energy shocks to the heart, interrupting the tachyarrhythmia or fibrillation and allowing the heart to resume a normal rhythm.

In CRM systems that include sensing channels for sensing one or more heart chambers, the ventricular and/or atrial sensing channels may be blanked or rendered refractory following certain events, such as following delivery of a pacing pulse. During the blanking or refractory periods, cardiac events are not sensed by the sensing channel, or sensed events are ignored or used differently than cardiac events sensed during other periods. Sensing channels are typically blanked after pacing to prevent reentry of an output pacing pulse into the system. Sensing channels may be rendered refractory to prevent misinterpretation of input data due to sensing after potentials or crosstalk between sensing channels.

The present invention involves enhanced methods and systems for managing refractory periods for single and multi-chamber pacing and provides various advantages over the prior art.

SUMMARY OF THE INVENTION

The present invention is directed to management of refractory periods during pacing. One embodiment of the invention involves a method for managing refractory periods during a cardiac cycle. The method includes pacing a heart and detecting an evoked response. At least one refractory period is adapted based on the detected evoked response. Adapting the refractory period may involve, for example, initiating the refractory period, terminating the refractory period, extending the refractory period or modifying one or more parameters of the refractory period. According to one aspect of the invention, adapting the refractory period involves modifying a sensing threshold based on the detected evoked response. The sensing threshold of an atrial sensing channel may be adjusted, for example, to avoid sensing a ventricular evoked response on the atrial channel while allowing sensing of a P-wave on the atrial channel. According to various implementations, adapting the refractory period may involve, for example, adapting a cross chamber or same chamber refractory period.

In accordance with a more particular embodiment of the invention, a method for managing refractory periods involves delivering a pacing pulse to a ventricle and detecting the evoked response of the ventricle. At least one post ventricular atrial refractory period is adapted based on the detected ventricular evoked response.

In accordance with another more particular embodiment, pacing pulses are delivered to right and left ventricles. One or more of a right ventricular evoked response and a left ventricular evoked response are detected. At least one refractory period is adapted based on the right ventricular evoked response or the left ventricular evoked response. In one implementation, a first atrial refractory period may be adapted relative to the right ventricular evoked response. A second atrial refractory period may be adapted relative to the left ventricular evoked response. In various implementations, an atrial refractory period may be adapted based on an evoked response associated with a first paced ventricle or may be adapted based on an evoked response associated with a last paced ventricle, for example.

Another embodiment of the invention is directed to a medical device. The medical device includes a plurality of electrodes configured to electrically couple to a heart. A pulse generator generates pacing pulses deliverable to the heart through the plurality of electrodes. Sensing circuitry is configured to detect electrical activity of the heart including at least one evoked response of the heart. Refractory management circuitry adapts at least one refractory period based on the detected evoked response.

In a more particular embodiment, the pulse generator is configured to generate a pacing pulse deliverable to a ventricle and the sensing circuitry is configured to detect an evoked response of the ventricle. The refractory management circuitry adapts at least one atrial refractory period relative to the detected ventricular evoked response.

In another more particular embodiment, the plurality of electrodes includes first electrodes electrically coupled to a right ventricle and second electrodes electrically coupled to a left ventricle. The pulse generator is configured to generate pacing pulses deliverable to the left and right ventricles. The sensing circuitry detects an evoked response of at least one of the left and right ventricles. The refractory management circuitry adapts at least one refractory period relative to the detected ventricular evoked response.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
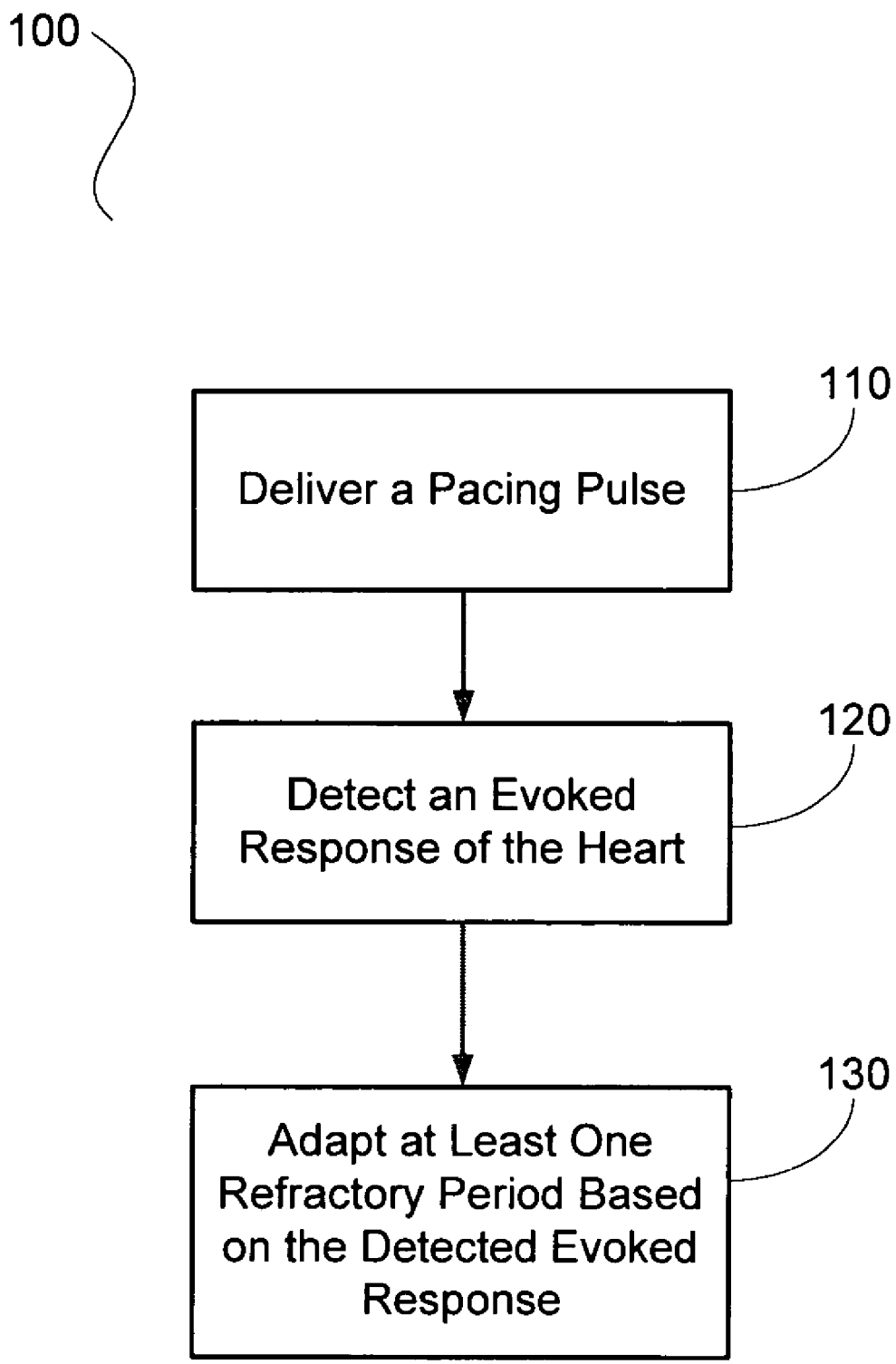
FIG. 1 is a flow chart of a method for managing refractory periods in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized in accordance with the invention, and structural and functional changes may be made without departing from the scope of the present invention.

Refractory periods are typically implemented after pacing to prevent unwanted sensing of signals related to the pace, e.g., the pacing output, pacing artifact, and/or crosstalk noise related to pacing. It is desirable to control the duration of the refractory periods to prevent misinterpretation of signals related to the pace, while allowing detection of other signals, such as intrinsic depolarizations of a tachyarrhythmic episode. The present invention is directed to approaches for managing refractory periods following pacing. In accordance with various approaches described herein, management of the refractory periods is based on detection of an evoked response associated with capture of the heart following pacing.

Immediately following delivery of a pacing pulse to a cardiac chamber, refractory periods or blanking periods are typically implemented on all sense channels to prevent swamping the input amplifiers of the sense channels by the electrical signal generated by the pacing pulse. The refractory or blanking periods may be same-chamber or cross-chamber implementations. Same-chamber refractory or blanking periods are initiated on the sense channel of the paced chamber. Cross-chamber refractory periods are initiated on sense channels other than the sense channel of the paced chamber. Sensing for a cardiac response to a pacing pulse generally follows an absolute refractory period or blanking period that immediately follows the pacing pulse.

Blanking and absolute refractory periods refer to different implementations that are typically used to alter the operation of a sense channel during the period of time that the relatively high level signal generated by the pace pulse is present on the sense channel inputs. During a blanking period, the inputs of the sense amplifier are shorted to prevent sensing. During absolute refractory periods, sensing may continue, but sensed events are ignored.

The system may also implement relative refractory periods, where sensed events may not be ignored, but the system's response to a sensed event is different from the system's response to an event sensed during a normal or non-refractory period. The system may implement relative refractory periods having a variable or dynamic sensing threshold, wherein a cardiac event associated with a signal amplitude below a threshold is ignored and a cardiac event associated with a signal amplitude above a threshold is detected and may be used for various purposes. The term "refractory period" is used generically herein to refer to a blanking period, a refractory period having a variable threshold, an absolute refractory period, a relative refractory period or combinations thereof.

Management of refractory periods after pacing may be desired to enhance detection of cardiac rhythm irregularities while the heart is being paced. For example, detection of atrial tachyarrhythmia may involve detecting the number of A-A intervals that fall into one or more atrial tachyarrhythmia rate zones. If an A-A interval is not sensed due to an atrial event occurring during a blanking or refractory period, undersensing of atrial events occurs. Undersensing atrial events may cause failure or delays in satisfying rate zone detection counters used in detection of atrial tachyarrhythmia. Further, the long A-A intervals caused by atrial undersensing may cause errors in the classification of types of atrial tachyarrhythmia, e.g., atrial fibrillation vs. atrial flutter. Failure to accurately detect atrial events may cause delays in implementation of atrial tachyarrhythmia therapy and/or inappropriate mode switching. For example, atrial undersensing may cause delays in mode switching or oscillations in switching back and forth between atrial tracking mode and atrial non-tracking mode. The problems associated with atrial undersensing may be reduced by managing refractory periods based upon detection of evoked responses in accordance with various exemplary embodiments of the invention described below.

Adapting a refractory period relative to an evoked response according to the invention allows for an increased period of sensing following a pacing pulse. In some implementations of the present invention, sensing may occur during a period of time after the pacing pulse but before an evoked response. The approaches described herein are particularly useful in cardiac rhythm management (CRM) devices that require atrial sensing in the presence of ventricular pacing, and also are particularly advantageous in systems implementing bi-ventricular pacing.

FIG. 1 is a flow chart of a method 100 for managing refractory periods in accordance with embodiments of the present invention. A pacing pulse is delivered 110 to heart. An evoked response to the pacing pulse is detected 120. At least one refractory period is adapted 130 based on the detected evoked response. A refractory period may be adapted by starting the refractory period, stopping the refractory period already in progress, extending the refractory period, or modifying one or more parameters of the refractory period, for example.

Figure 2A:
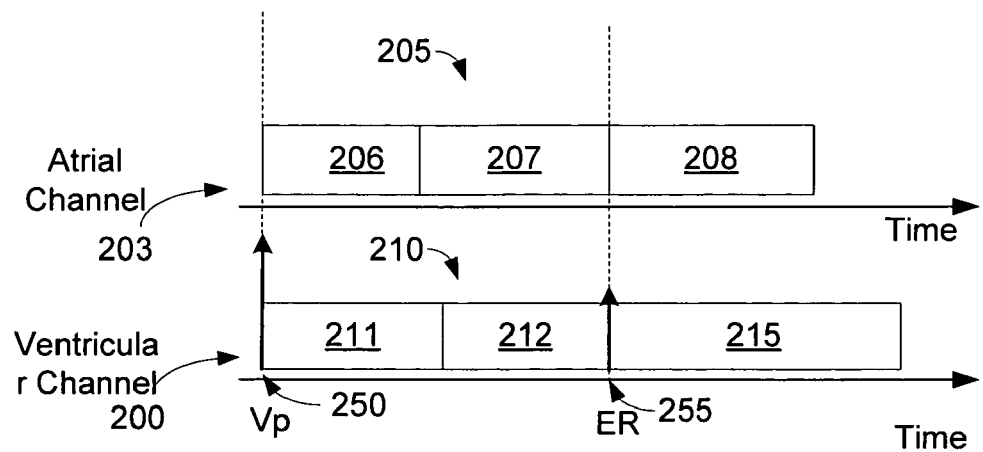
FIGS. 2A-2B are timing diagrams illustrating management of refractory periods based on detection of an evoked response in accordance with embodiments of the invention.

FIG. 2A depicts implementation of refractory periods in a dual chamber device in accordance with embodiments of the invention. FIG. 2A shows refractory periods implemented following a pacing pulse to the ventricle. The refractory periods are implemented for a ventricular sensing channel 200 sensing electrical activity of the ventricle and an atrial channel 203 sensing electrical activity of an atrium. After the heart is paced, a ventricular refractory period (VRP) 210 is initiated on the ventricular sensing channel 200. A post ventricular atrial refractory period (PVARP) 205 is initiated on atrial channel 203.

The VRP 210 and/or the PVARP 205 may include one or more portions and each portion may use various sensing configurations. For example, the VRP 210 and/or the PVARP 205 may include one or more of a blanking period, an absolute refractory period, a relative refractory period, and a refractory period using a variable sensing threshold.

In one embodiment, absolute refractory periods 211, 206 are initiated on the ventricular sensing channel and the atrial sensing channel immediately following the pacing pulse 250. The absolute refractory periods 211, 206 may continue, for example, until the electrical artifact associated with the ventricular pacing pulse dissipates and/or the pacing recharge pulse completes. The absolute refractory periods 211, 206 are followed by relative refractory periods 212, 207.

The relative refractory period 212 on the ventricular channel allows the detection of the beginning of the evoked response (ER) 255 by the ventricular sensing channel. Alternatively, the evoked response 255 may be sensed using an evoked response sensing channel or other sensing channel that is separate from the ventricular sensing channel.

The relative refractory period 208 on the atrial channel allows the system to sense for atrial events associated with aberrant atrial rhythms, e.g., atrial tachyarrhythmia or fibrillation.

Upon sensing the beginning of the evoked response 255, the system may adapt ventricular and atrial refractory periods 210, 205. For example, the system may extend one or more refractory periods, e.g., extend one or both of the VRP and/or the PVARP, after sensing the beginning of the evoked response. In the example illustrated in FIG. 2A, the system extends the VRP 210 and PVARP 205 for additional time periods 215, 208. The extended VRP 215, may comprise a relative refractory period wherein the system interprets the sensed ventricular signals in a certain way, i.e., as cardiac signals responsive to a pacing pulse. The extended PVARP 208, may prevent misinterpreting a sensed far-field evoked response as a P-wave.

Figure 3A:
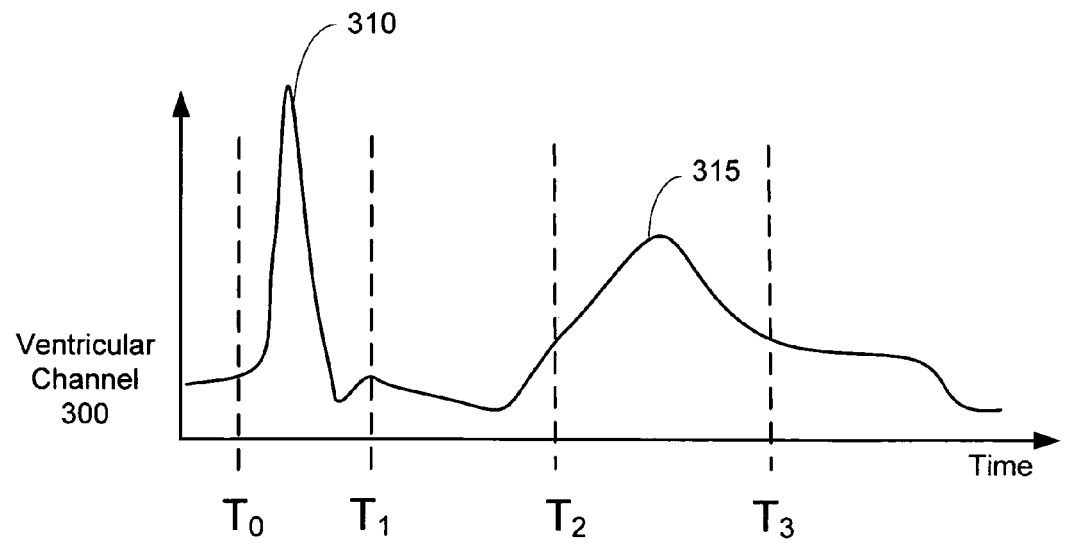
FIGS. 3A and 3B illustrate the use of a variable sensing threshold during a post ventricular atrial refractory period in accordance with embodiments of the invention.
Figure 3B:
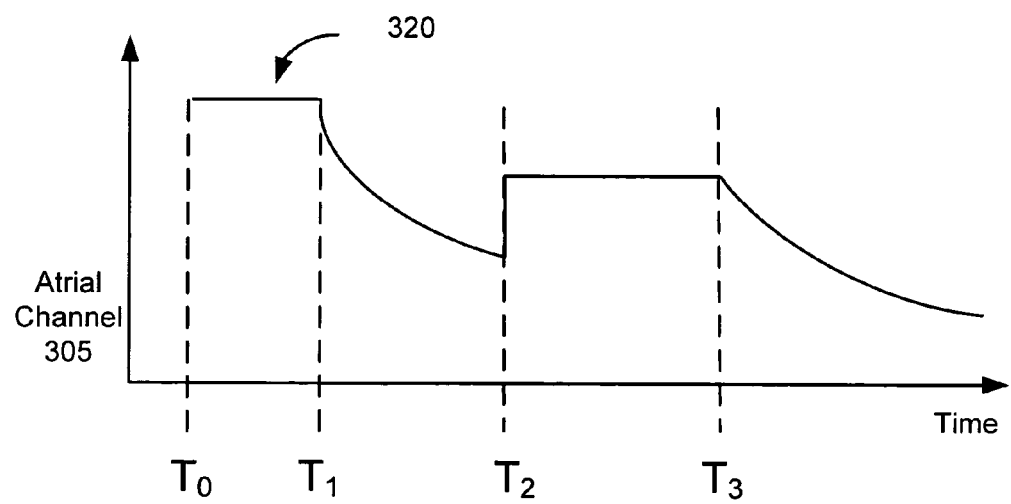

The VRP and/or PVARP extension periods 215, 208 may continue, for example, until the end of an evoked response detection interval. Alternatively, the duration of the VRP and/or PVARP extension periods 215, 208 may continue for a predetermined period other than the evoked response detection interval, or extended until a certain event is sensed, such as a return to a nominal sensed value following detection of the evoked response, for example. The termination of the PVARP 205 and the VRP 210 need not be coincident. The PVARP 205 may extend past the VRP 210 or the reverse. The sensing thresholds used during the PVARP 205 and/or VRP 210 may vary. FIGS. 3A and 3B illustrate one implementation of a variable sensing threshold.

Figure 2B:
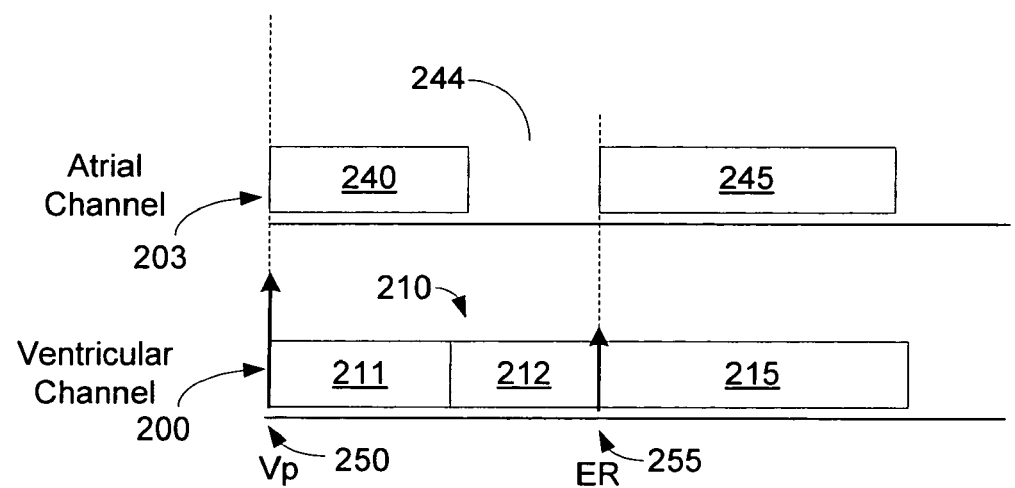

FIG. 2B provides another illustration of refractory period(s) that are adapted based on a sensed evoked response. In this implementation, absolute refractory periods 211, 240 are initiated on ventricular 200 and atrial 203 sensing channels, respectively, following a pacing pulse 250. The absolute refractory periods 211, 240 may continue until a recharge period has been completed or for other time intervals. In the example illustrated in FIG. 2B, a relative ventricular refractory period 212 follows the absolute refractory period 211 on the ventricular channel 200. The first PVARP 240 ends after a period of time and atrial sensing returns to normal mode during time period 244. A second PVARP 245 is initiated upon sensing the beginning of the evoked response 255. The evoked response 255 may be sensed using the ventricular sensing channel 200, using an evoked response channel, or using another sensing channel, for example.

In various implementations, refractory periods for ventricular and/or atrial sensing channels may be initiated, terminated, extended or modified based on the detection of the beginning of an evoked response. In the example of FIG. 2B, the detection of evoked response 255 terminates normal atrial sensing and a second PVARP 245 is initiated on the atrial channel to prevent sensing the far-field evoked response as a P-wave.

In accordance with embodiments of the invention, relative ventricular refractory period 212, extended ventricular refractory period 215, the first PVARP 240 and/or second PVARP 245 may include a variable sensing threshold as described below in connection with FIG. 3.

With respect to atrial sensing on atrial channel 203, in both examples 2A and 2B provided above, atrial sensing may resume shortly after a pacing pulse is delivered and may continue until the evoked response 255 is sensed. In this way, atrial sensing may be suspended for only a short period of time following pacing allowing atrial channel 203 flexibility in sensing between a pace pulse 250 and an evoked response 255. Atrial channel 203 may be in a non-refractory or relative refractory state for as long as possible between the pace pulse and the detection of the evoked response. This scenario is compared to previous implementations, wherein the atrial channel remains refractory through the end of the worst-case evoked response for all patients. Modifying the PVARP, or terminating the PVARP and initiating a second PVARP 245 on atrial channel 203 allows the system to adapt to the occurrence of the evoked response in a given patient. The present invention may be particularly advantageous when used in cardiac devices having shorter pacing recharge times, where the analog blanking period may be complete well before the evoked response occurs. Adapting the refractory periods to accommodate individual patient responses may provide for enhanced sensing of atrial events in the presence of ventricular pacing. Furthermore, enhanced atrial sensing may enable accurate pacing mode switches and may improve atrial tachyarrhythmia detection and atrial rhythm classification.

FIGS. 3A and 3B illustrate the use of a variable sensing threshold during a post ventricular atrial refractory period in accordance with embodiments of the invention. FIG. 3A illustrates the electrical signal present on the ventricular channel 300 following a pacing pulse delivered at $T_0$ that captures the ventricular chamber. The first peak 310 is produced by the pacing pulse and the second peak 315 is produced by the evoked response. Corresponding FIG. 3B is a diagram illustrating the variable sensing threshold 320 used on an atrial channel 305 in accordance with embodiments of the invention. When the pacing pulse is delivered at time $T_0$, the sensing threshold 320 is raised to a relatively high (or absolute) level so that the electrical signal associated with the ventricular pace is not sensed on the atrial channel. At time $T_1$, a relative atrial refractory period begins, and the sensing threshold 320 on the atrial channel begins to gradually decrease to allow for increased sensing of intrinsic atrial events. In some embodiments, the sensing threshold may decrease to a normal sensing threshold prior to time $T_2$, thus ending the atrial refractory period initiated by the pacing pulse. This scenario is described above in connection with FIG. 2B.

When the evoked response signal 315 is detected on ventricular channel 300, at time $T_2$, the gradually decreasing sensing threshold 320 is re-set to an elevated threshold. The elevated threshold may be set high enough so that an evoked response from the ventricle is not sensed on the atrial sensing channel 305 but allows sensing of a P-wave. At time $T_3$, which may coincide with a decreasing evoked response signal 315 on ventricular channel 300, the atrial channel 305 sensing threshold begins to gradually decrease to a normal sensing threshold.

Examples of systems and methods implementing cross-chamber refractory periods including variable sensing thresholds are described in commonly owned U.S. Pat. No. 6,169,918 and U.S. Pat. No. 6,928,323, which are incorporated herein by reference in their respective entireties.

Figure 4:
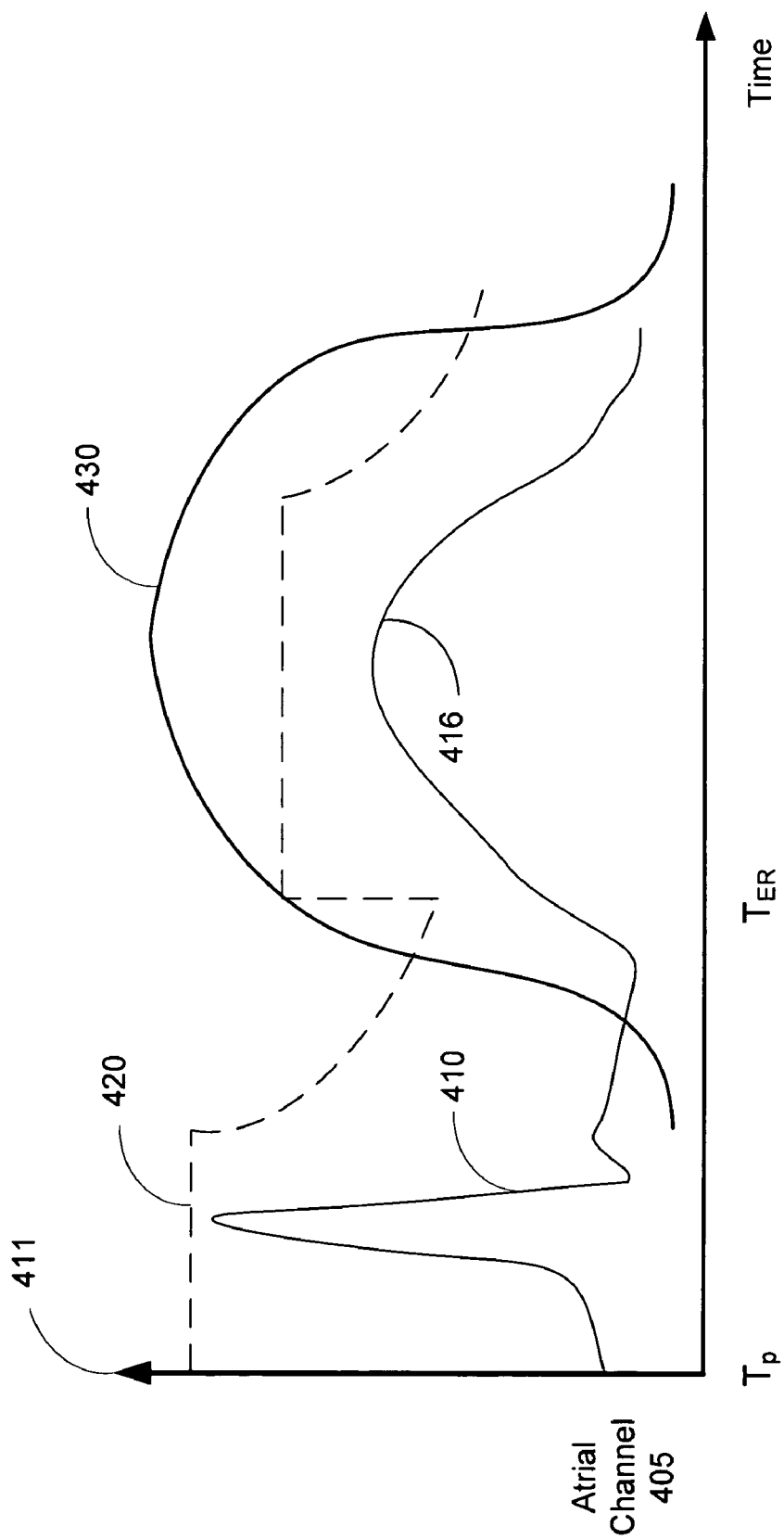
FIG. 4 is a diagram of superimposed graphs showing the ventricular pacing pulse artifact and the ventricular evoked response, a P-wave, and a variable sensing threshold implemented during one or more atrial refractory periods in accordance with embodiments of the invention.

FIG. 4 is a diagram showing superimposed graphs of the ventricular pacing pulse artifact 410 and the ventricular evoked response 416 as sensed on the atrial channel 405, a P-wave 430 sensed on the atrial channel, and a variable sensing threshold 420 implemented in accordance with embodiments of the invention. As previously described, the sensing threshold 420 of the atrial channel is modified upon detection of an evoked response. Modification of the sensing threshold may alter a refractory period already in progress or initiate a new refractory period if the sensing threshold has returned to a normal level, ending a previously initiated refractory period. The modified sensing threshold allows for enhanced detection of a P-wave 430 while avoiding the detection of the ventricular evoked response 416 sensed on the atrial channel.

In this implementation the sensing threshold 420, as previously illustrated in FIG. 3B, is elevated at time $T_p$ when a pacing pulse is delivered and then gradually decreases. The initially high sensing threshold following the pacing pulse is used to avoid sensing the ventricular pacing artifact 410. Upon detection of the evoked response at time $T_{ER}$ the sensing threshold is again increased to avoid sensing the evoked response 416 on the atrial channel. The level of the sensing threshold is selected to avoid sensing the evoked response 416, but to allow P-waves 430 to be sensed. Modification of the sensing threshold based on the evoked response in accordance with embodiments of the invention provides for an increased window of opportunity for sensing P-waves 430 following a ventricular pace 411.

Management of refractory periods after pacing based on detection of an evoked response is particularly advantageous when used in bi-ventricular pacing implementations. Bi-ventricular pacing involves delivering pacing pulses to right and left ventricles, wherein the pacing pulses may be separated in time by a interventricular delay (IVD) which could extend up to about 50 ms or longer. If atrial sensing is prevented by a PVARP that extends throughout the bi-ventricular pacing period and until after the worst case evoked response timing from the last paced ventricle has completed, the probability that atrial events will be undersensed is increased significantly. Embodiments of the present invention are directed to management of atrial refractory periods based on sensing evoked responses during bi-ventricular pacing.

Figure 5:
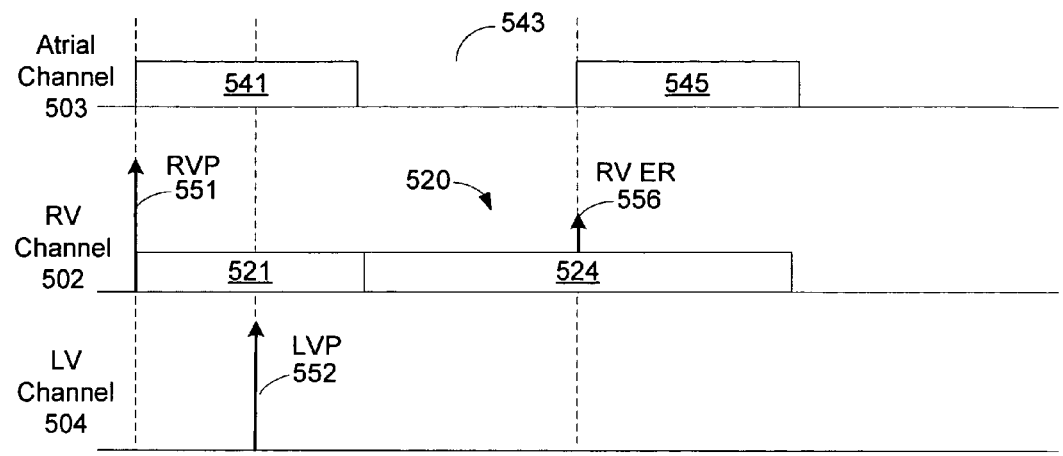
FIGS. 5-7 are timing diagrams depicting the management of refractory periods during bi-ventricular pacing in accordance with embodiments of the invention.
Figure 6:
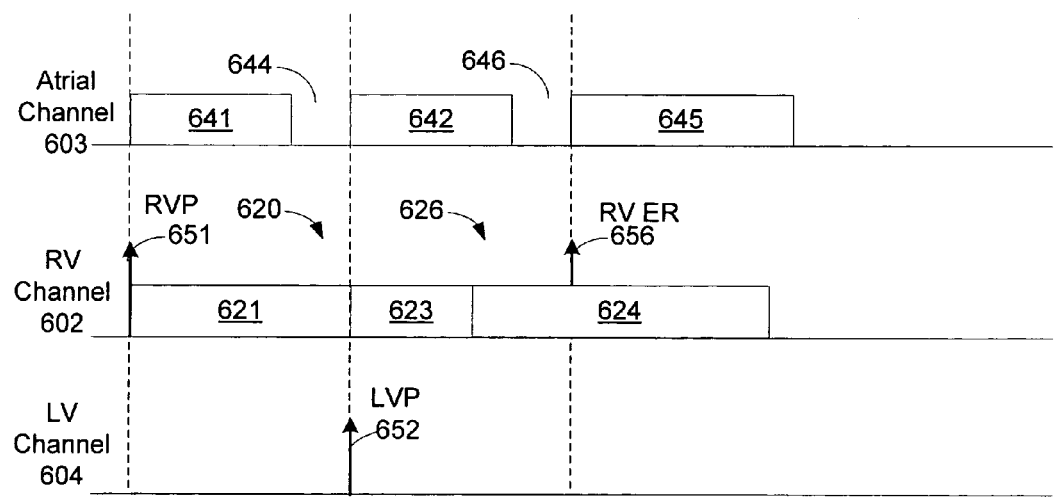
Figure 7:
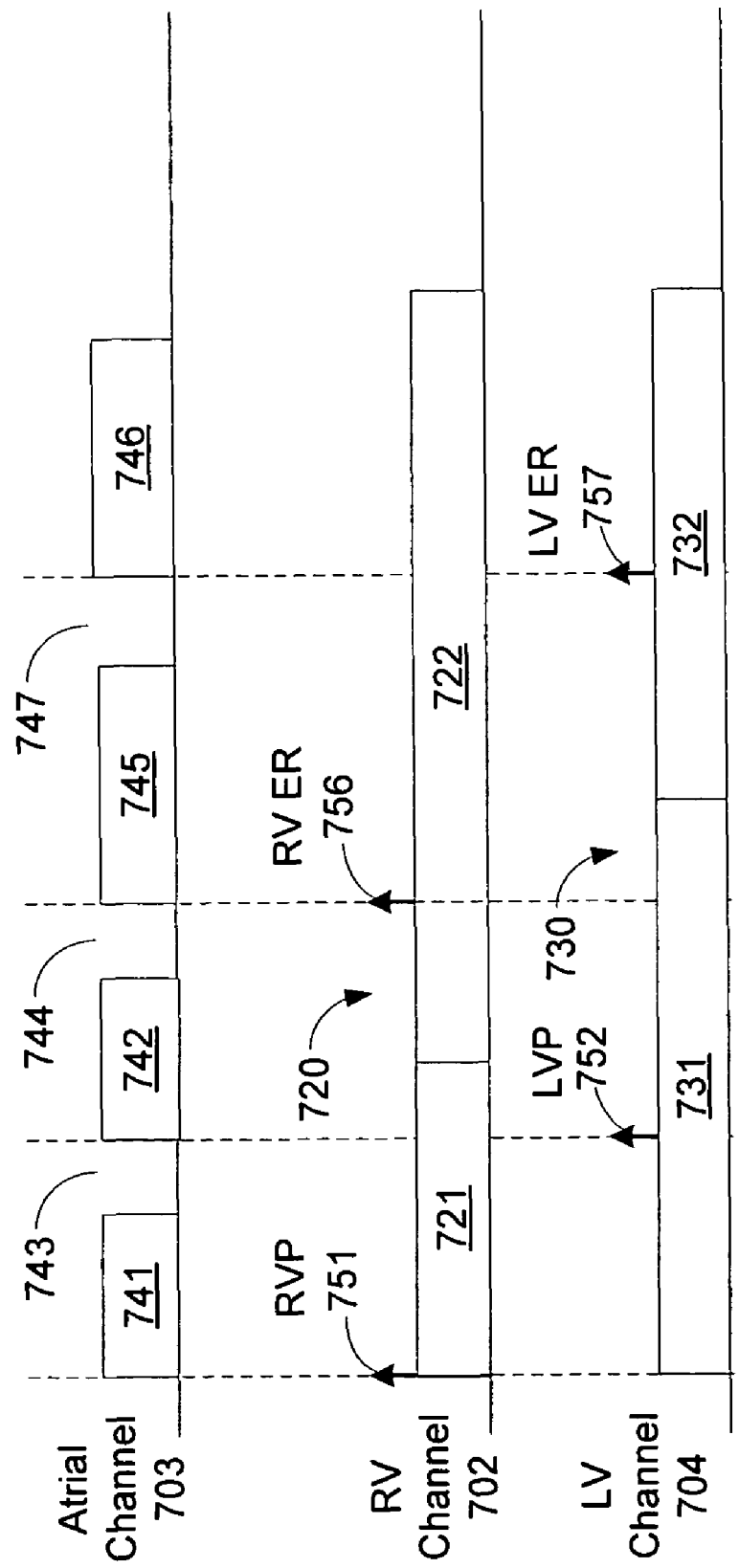

FIGS. 5-7 illustrate timing diagrams depicting the management of refractory periods during bi-ventricular pacing in accordance with embodiments of the invention. Initiating a refractory period on an atrial channel in response to a right or left ventricular pace and then adapting the refractory period based on an evoked response increases the time available for sensing atrial events that would otherwise be unavailable.

Turning to FIG. 5, timing diagrams for refractory periods associated with a right ventricular (RV) sensing channel 502, left ventricular (LV) sensing channel 504, and an atrial sensing channel 503, respectively, are depicted. In this embodiment, no sensing occurs in the left ventricle and the IVD is relatively short. When a pace pulse 551 is delivered to the right ventricle, refractory periods 520 and 541 are initiated on the RV channel 502 and atrial channel 503, respectively. As previously described, the refractory periods 520, 541 may include one or more of a blanking portion, an absolute refractory portion, a relative refractory portion, and a variable sensing portion.

In this particular implementation, the ventricular refractory period 520 on RV channel 502, includes an absolute refractory portion 521 that extends at least from the time of the first pace, RV pace 551 in this example, through the second pace, LV pace 552, and for a period of time sufficient to allow the pacing artifacts from the RV and LV paces 551, 552 to dissipate. The ventricular refractory period 520 includes a relative refractory portion 524. The relative refractory portion 524 of the VRP 520 allows the detection of an RV evoked response (RV ER) 556.

On the atrial channel 503, an absolute PVARP 541 is initiated responsive to the RV pacing pulse 551. The PVARP 541 extends through the LVP 552 and may continue, for example, until the pacing artifacts from the RV and LV paces 551, 552, dissipates. In the implementation illustrated in FIG. 5, the PVARP 541 terminates after a predetermined time period to allow enhanced atrial sensing during period 543. Alternatively, the PVARP may not terminate, but the sensing threshold of the atrial refractory period may decrease to allow enhanced atrial sensing during period 543.

Sensing on atrial channel 503 is adapted based on the detection of the RV evoked response (RV ER) 556. If the previous PVARP 541 has terminated, a second PVARP 545 due to RV ER 556 may be initiated. Alternatively, the sensing threshold of the atrial channel may be increased during period 545 to avoid sensing the far-field evoked response signal but to allow sensing P-waves during this period 545.

FIG. 6 illustrates timing diagrams for refractory periods implemented on sensing channels of a bi-ventricular device in accordance with an embodiment of the invention. In this embodiment, no sensing occurs in the left ventricle and the IVD is long enough to allow atrial sensing between delivery of the right and the left pacing pulses. An absolute ventricular refractory period 621 is initiated on RV sensing channel 602 and an absolute atrial refractory period 641 is initiated on the atrial sensing channel 603 in response to a right ventricular pulse (RVP) 651. The sensing threshold of the atrial channel 603 may return to normal after a period of time, ending the atrial refractory period 641 and allowing atrial sensing during the period 644 between the right and left ventricular paces. Alternatively, the sensing threshold of the atrial channel 603 may be variable, decreasing prior to the left ventricular pulse (LVP) 652, and allowing atrial sensing during the period 644.

The ventricular refractory period 621 may be extended or a new ventricular refractory period 626 initiated in response to the left ventricular pace (LVP) 652. The ventricular refractory period 626 includes an absolute refractory portion 623 and a relative refractory portion 624. The relative refractory portion 624 allows the device to sense for an evoked response 656 to the RVP 651.

A second absolute atrial refractory period 642 is initiated on the atrial channel 603 in response to the LVP 652. The sensing threshold of the atrial channel 603 may return to normal after a period of time, ending the atrial refractory period 642. Alternatively, a variable sensing threshold may decrease so that atrial sensing occurs during the period 646 between the LVP and the beginning of the right ventricular evoked response 656.

When the beginning of right ventricular evoked response 656 is detected, the sensing threshold of the atrial channel 603 is raised, initiating a new refractory period 645 or extending the previous refractory period. Refractory period 645 may have a variable sensing threshold that avoids sensing of the far field evoked response, but allows sensing of P-waves during this period 645.

FIG. 7 shows timing diagrams illustrating the management of refractory periods in a bi-ventricular device in accordance with a further embodiment of the invention. In this embodiment, pacing occurs in both left and right ventricles, sensing occurs in both left and the right ventricular channels and evoked responses may be detected for both left and right ventricles.

Ventricular refractory periods 720, 730 are initiated on RV channel 702 and LV channel 704, respectively, in response to a RVP 751. The ventricular refractory periods 720, 730 include absolute refractory portions 721, 731 that are implemented immediately after the RVP 751.

An absolute atrial refractory period 741 is initiated on the atrial channel 703 in response to the RVP 751. The sensing threshold of the atrial channel 703 may return to normal after a period of time, ending the atrial refractory period 741 and allowing atrial sensing during the period 743 between the right and left ventricular paces 751, 752. Alternatively, the sensing threshold of the atrial channel 703 may be variable, decreasing gradually prior to the LVP 252, and allowing atrial sensing during the period 743.

The absolute ventricular refractory portions 721, 731 of ventricular refractory periods 720, 730 may be extended or new absolute ventricular refractory portions may be initiated in response to the LVP 252. A second absolute atrial refractory period 742 is initiated on the atrial channel 703 in response to the LVP 752. The sensing threshold of the atrial channel 703 may return to normal or may be decreased gradually after a period of time, ending the atrial refractory period 742 and allowing atrial sensing during the period 744 between the left ventricular pace 752 and the beginning of the right ventricular evoked response 756.

The right ventricular refractory period 720 includes a relative refractory portion 722 to allow the device to sense for a right ventricular evoked response 756. The left ventricular refractory period 730 includes a relative refractory portion 732 to allow the device to sense for a left ventricular evoked response 757.

Upon sensing the right ventricular evoked response 756, an atrial refractory period 745 is initiated or the sensing threshold of the atrial channel is increased to avoid sensing the far-field evoked response of the right ventricle. The sensing threshold may be selected so that intrinsic P-waves can be sensed during this period 745. After a period of time, the sensing threshold may decrease or return to normal 747 between detection of the right and left evoked responses 756, 757, to allow normal sensing of atrial events.

Upon sensing the left ventricular evoked response 757, an atrial refractory period 746 is initiated or the sensing threshold of the atrial channel is increased to avoid sensing the far-field evoked response of the left ventricle. The sensing threshold may be selected so that intrinsic P-waves can be sensed during this period 746.

FIGS. 5-7 illustrate representative examples of refractory period management for bi-ventricular pacing. Many possible arrangements are possible in addition to these exemplary embodiments. For example, in one implementation, sensing may occur in both ventricles, but an atrial refractory period may be adapted based on only one detected evoked response (left or right ventricle). In another implementation, for example, an atrial refractory period may be adapted based on the evoked response of a first paced ventricle or a last paced ventricle. In another implementation, an atrial refractory period may be adapted based on a first detected ventricular evoked response or a last detected ventricular evoked response.

Although the examples of FIGS. 5-7 show pacing the right ventricle before pacing the left ventricle, the ventricles may be paced in the opposite order or may be paced substantially simultaneously. For left ventricle first pacing, refractory periods may be adapted based on one or more of a left ventricular evoked response and a right ventricular evoked response in a similar approach to the examples illustrated herein.

The example timing diagrams provided above in FIGS. 2A, 2B, and 5-7 and the variable sensing threshold depicted in FIGS. 3A and 3B represent examples of the many possible implementations of the present invention for managing refractory periods based on detection of evoked responses. The approaches described herein may be implemented to adapt refractory periods, including same chamber and/or cross chamber refractory periods based on detection of an evoked response, such as by terminating a refractory period, initiating a refractory period, extending a refractory period, modifying one or more refractory period parameters, altering sensing thresholds during a refractory period, or by any other process that alters a refractory period based on the detection of an evoked response.

Figure 8:
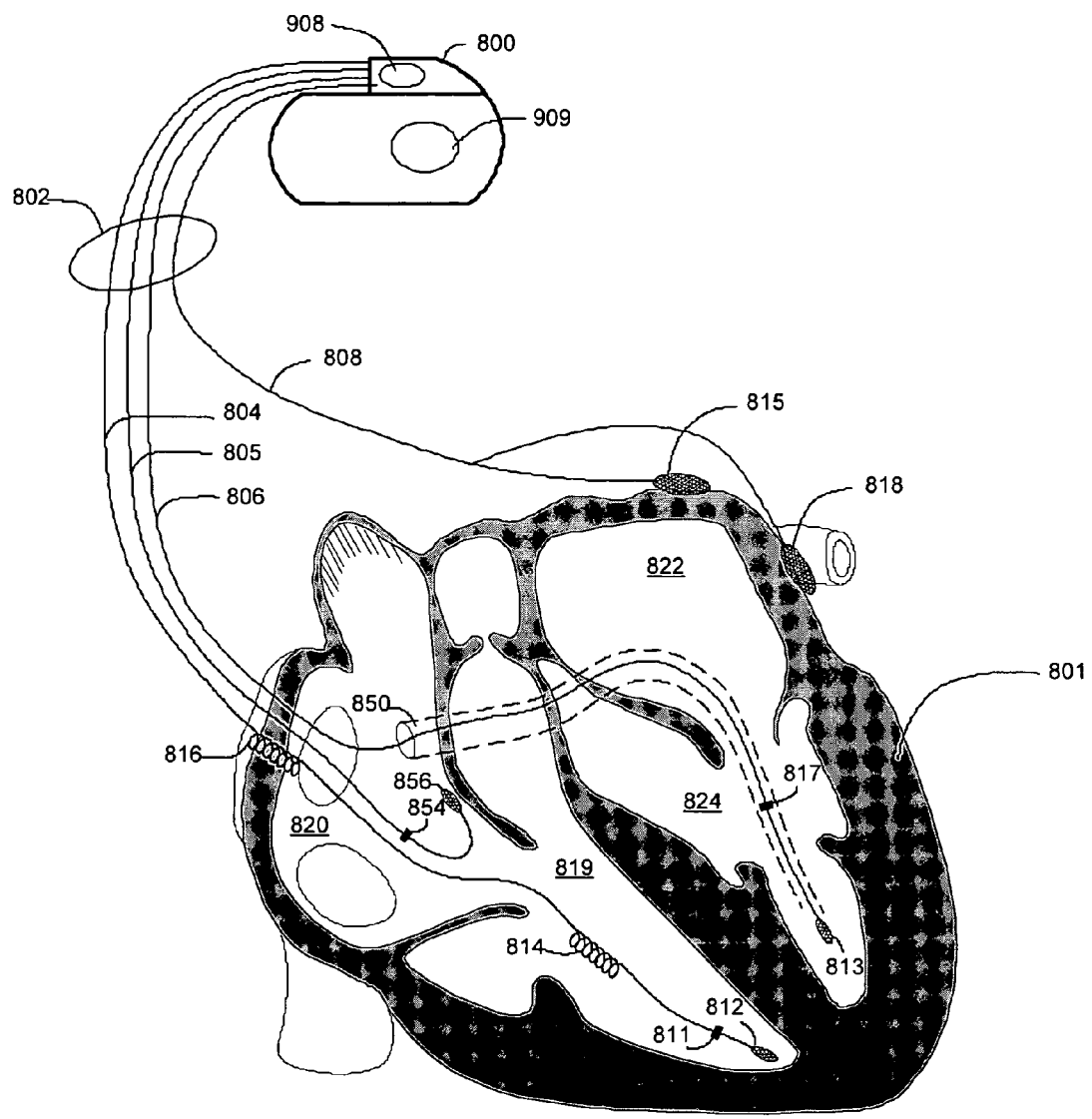
FIG. 8 is a partial view of one embodiment of an implantable medical device in accordance with embodiments of the invention.

Referring now to FIG. 8 of the drawings, there is shown a cardiac rhythm management system that may be used to implement refractory period management in accordance with the present invention. The cardiac rhythm management system illustrated in FIG. 8 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 includes electrodes used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 8, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 8 illustrates one embodiment that may be used in connection with the pacing and sensing methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 8, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 8 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 8 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 9:
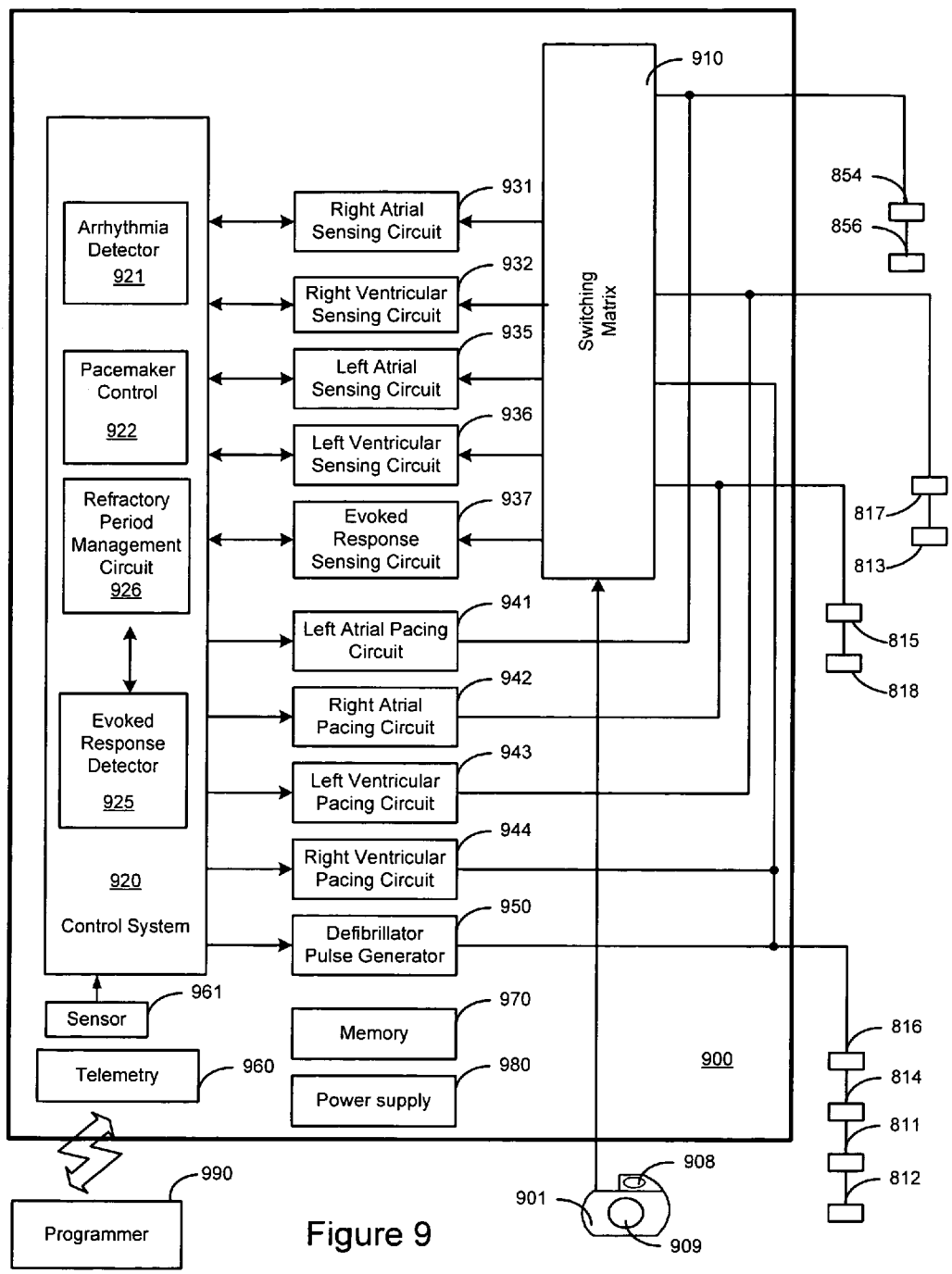
FIG. 9 is a block diagram of an implantable medical device that may be used to manage refractory periods in accordance with embodiments of the invention.

Referring now to FIG. 9, there is shown a block diagram of a cardiac pacemaker/defibrillator 900 suitable for implementing refractory period management methods of the present invention. FIG. 9 shows a cardiac pacemaker/defibrillator 900 divided into functional blocks. It is understood by those skilled in the art that there exist many possible configurations in which these functional blocks can be arranged. The example depicted in FIG. 9 is one possible functional arrangement. Other arrangements are also possible. For example, more, fewer or different functional blocks may be used to describe a cardiac pacemaker/defibrillator suitable for implementing the methodologies for refractory period management in accordance with the present invention. In addition, although the cardiac pacemaker/defibrillator 900 depicted in FIG. 9 contemplates the use of a programmable microprocessor-based logic circuit, other circuit implementations may be utilized.

The cardiac pacemaker/defibrillator 900 depicted in FIG. 9 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may be used store parameters for various pacing and sensing modes, along with other parameters. The memory 970 may be used, for example, for storing historical EGM and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system 920 depicted in FIG. 7 incorporates an evoked response detector 925. The control system 920 also includes refractory period management circuitry 926. The refractory period management circuitry 926 adapts refractory periods of one or more of the sensing circuits 931, 932, 935, 937, based on detection of an evoked response as determined by the evoked response detector 925 in accordance with embodiments of the invention. The control system 920 includes additional functional components including a pacemaker control circuit 922, and may include an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990 or other remote system. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, commands may be transferred to the control system 920 of the cardiac pacemaker/defibrillator 900 from the programmer unit 990 during and after implant. In addition, stored cardiac data may be transferred to the programmer unit 990 from the cardiac pacemaker/defibrillator 900. The telemetry circuitry 960 may provide for communication between the cardiac pacemaker/defibrillator 900 and an external medical records or information system as previously described.

In the embodiment of the cardiac pacemaker/defibrillator 900 illustrated in FIG. 9, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. A bipolar right ventricular signal may be sensed as a voltage developed between the RV-tip 812 and the RV-ring 811. Alternatively, bipolar sensing in the right ventricle may be implemented using the RV-tip electrode 812 and the RV-coil 814. Unipolar sensing in the right ventricle may be implemented, for example, by sensing voltages developed between the RV-tip 812 and the can electrode 909.

Right ventricular cardiac signals may also be sensed through use of the defibrillation electrodes. More particularly, a right ventricular signal may be detected as a voltage developed between the RV-coil 814 and the SVC-coil 816. A right ventricular signal may also be detected as a voltage developed between the RV-coil 814 and the can electrode 909. In another configuration the can electrode 909 and the SVC-coil electrode 816 may be electrically shorted and a right ventricular signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 may be used to sense and amplify voltages developed using various combinations of electrodes to facilitate detection of evoked responses used for management of refractory periods in accordance with embodiments of the invention. Evoked responses may alternatively be detected through the use of the sensing circuits 931, 932, 935, 936 associated with particular heart chambers. The capture detector 925 analyzes the output of the evoked response sensing circuit 937 or other sensing circuits 931, 932, 935, 936 to detect an evoked response. The results of the evoked response detection may be used by the refractory period management circuit 926 to manage refractory periods of one or more of the sensing circuits 931, 932, 935, 936.

Various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing for evoked response detection. In other embodiments, the same electrode combination is used for pacing and sensing for an evoked response.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above. In some implementations, the cardiac pacemaker/defibrillator 900 may include a sensor 961 that is used to sense the patient's hemodynamic need. The timing of the pacing pulses may be adjusted to respond to the patient's hemodynamic need based on the sensor 961 output.

Various modifications and additions may be made to the embodiments discussed herein without departing from the scope of the present invention. Accordingly, the scope of the present invention should not be limited by the particular embodiments described above, but should be defined only by the claims set forth below and equivalents thereof.

The invention claimed is:

1. A method of managing refractory periods implemented during a cardiac cycle, comprising:
   delivering a pacing pulse to a heart;
   initiating a refractory period following the pacing pulse;
   detecting an evoked response;
   extending or re-initiating the refractory period in response to detecting the evoked response; and
   modifying a sensing threshold of a previously initiated refractory period based on the detected evoked response.

2. The method of claim 1, wherein modifying the sensing threshold comprises increasing the sensing threshold based on the detected evoked response.

3. The method of claim 1, wherein:
   delivering a pacing pulse to the heart comprises delivering a pacing pulse to a first heart chamber; and
   extending or re-initiating the refractory period comprises extending or re-initiating a cross-chamber refractory period associated with a sensing channel of a second heart chamber.

4. The method of claim 1, wherein:
   delivering a pacing pulse to the heart comprises delivering a pacing pulse to a heart chamber; and
   extending or re-initiating the refractory period comprises extending or re-initiating a same-chamber refractory period associated with a sensing channel of the heart chamber.

5. A method of managing refractory periods implemented during a cardiac cycle, comprising:
   delivering pacing pulses to right and left ventricles of a heart;
   initiating an atrial refractory period following the pacing pulses;
   detecting one or more of a right ventricular evoked response and a left ventricular evoked response; and
   extending or re-initiating the atrial refractory period based on the right ventricular evoked response or the left ventricular evoked response.

6. The method of claim 5, wherein extending or re-initiating the atrial refractory period based on the right ventricular evoked response or the left ventricular evoked response comprises:
   extending or re-initiating a first atrial refractory period based on the right ventricular evoked response; and
   extending or re-initiating a second atrial refractory period based on the left ventricular evoked response.

7. The method of claim 5, wherein extending or re-initiating the atrial refractory period based on the right ventricular evoked response or the left ventricular evoked response comprises extending or re-initiating the atrial refractory period based on an evoked response associated with a first paced ventricle.

8. The method of claim 5, wherein extending or re-initiating the atrial refractory period based on the right ventricular evoked response or the left ventricular evoked response comprises extending or re-initiating the atrial refractory period based on an evoked response associated with a last paced ventricle.

9. The method of claim 5, wherein extending or re-initiating the atrial refractory period based on the right ventricular evoked response or the left ventricular evoked response comprises extending or re-initiating the atrial refractory period based on an evoked response associated with a first detected ventricular evoked response.

10. The method of claim 5, wherein extending or re-initiating the atrial refractory period based on the right ventricular evoked response or the left ventricular evoked response comprises extending or re-initiating the atrial refractory period based on an evoked response associated with a last detected ventricular evoked response.

11. The method of claim 5 further comprising, adjusting a sensing threshold of an atrial sensing channel to avoid sensing one or more of the right ventricular evoked response and the left ventricular evoked response on the atrial channel and to allow sensing of P-waves on the atrial channel.

12. The method of claim 11, wherein adjusting the sensing threshold comprises increasing the sensing threshold based on the detected one or more of the right ventricular evoked response and the left ventricular evoked response.

13. A medical device, comprising:
   a plurality of electrodes configured to electrically couple to a heart;
   a pulse generator configured to generate pacing pulses deliverable to the heart through the plurality of electrodes;
   sensing circuitry configured to detect electrical activity of the heart, the electrical activity including evoked responses of the heart responsive to the pacing pulses; and refractory management circuitry coupled to the sensing circuitry and configured to initiate a refractory period following a pacing pulse of a cardiac cycle and extend or re-initiate the refractory period in response to detecting an evoked response associated with the pacing pulse, wherein the refractory management circuitry is configured to modify the sensing threshold during the refractory period based on the detected evoked response.

14. The medical device of claim 13, wherein the refractory management circuitry is further configured to increase the sensing threshold based on the detected evoked response.

15. The medical device of claim 13, wherein refractory management circuitry is configured to implement a variable sensing threshold during the refractory period, wherein the variable sensing threshold is modified based on the detected evoked response.

16. A medical device, comprising:
first electrodes configured to electrically couple to a right ventricle and second electrodes configured to electrically couple to a left ventricle;
a pulse generator configured to generate pacing pulses deliverable to the left and right ventricles through the first and second electrodes;
sensing circuitry configured to detect at least one of a left ventricular evoked response and a right ventricular evoked response; and
refractory management circuitry coupled to the sensing circuitry configured to initiate an atrial refractory period following a pacing pulse of a cardiac cycle and extend or re-initiate the atrial refractory period based on one or both of the left ventricular evoked response and the right ventricular evoked response.

17. The medical device of claim 16, wherein:
the sensing circuitry is configured to detect both a right ventricular evoked response and a left ventricular evoked response; and
the refractory management circuitry is configured to extend or re-initiate the atrial refractory period based on one or more of the right ventricular evoked response and the left ventricular evoked response.

18. The medical device of claim 16, wherein the refractory management circuitry is further configured to extend or re-initiate the atrial refractory period based on an evoked response associated with a first paced ventricle.

19. The medical device of claim 16, wherein the refractory management circuitry is further configured to extend or re-initiate the atrial refractory period based on an evoked response associated with a last paced ventricle.

20. The medical device of claim 16, wherein the refractory management circuitry is further configured to extend or re-initiate the atrial refractory period based on an evoked response associated with a first detected ventricular evoked response.

21. The medical device of claim 16, wherein the refractory management circuitry is further configured to extend or re-initiate the atrial refractory period based on an evoked response associated with a last detected ventricular evoked response.

22. The method of claim 16, further comprising increasing a sensing threshold of a previously initiated refractory period based on the detected one or more of a right ventricular evoked response and a left ventricular evoked response.

23. A medical device for managing refractory periods, comprising:
a plurality of electrodes configured to electrically couple to a heart;
a pulse generator configured to generate pacing pulses deliverable to the heart through the plurality of electrodes;
means for managing refractory periods following the pacing pulses, including initiating a refractory period following a pacing pulse delivered during a cardiac cycle, wherein the means for managing the refractory period extends or re-initiates one or more atrial refractory periods based on one or more of a right ventricular evoked response and a left ventricular evoked response; and
means for detecting an evoked response associated with the pacing pulse, wherein the means for managing refractory periods extends or re-initiates the refractory period in response to detecting the evoked response.

24. The medical device of claim 23, wherein the means for managing the refractory periods increases a sensing threshold of the refractory period based on the detected evoked response.

* * * * *